United States Patent
Miranda et al.

(10) Patent No.: US 12,028,387 B2
(45) Date of Patent: Jul. 2, 2024

(54) METHOD OF ADDING LANGUAGE INTERPRETER DEVICE TO VIDEO CALL

(71) Applicant: Doximity, Inc., San Francisco, CA (US)

(72) Inventors: Bruno Paladini Miranda, San Diego, CA (US); Jey Balachandran, San Francisco, CA (US); Jeremiah Konoske, Davis, CA (US); Joel Davis, San Francisco, CA (US)

(73) Assignee: Doximity, Inc., San Francisco, CA (US)

( * ) Notice: Subject to any disclaimer, the term of this patent is extended or adjusted under 35 U.S.C. 154(b) by 0 days.

(21) Appl. No.: 17/713,146

(22) Filed: Apr. 4, 2022

(65) Prior Publication Data
US 2022/0329638 A1 Oct. 13, 2022

Related U.S. Application Data

(60) Provisional application No. 63/171,851, filed on Apr. 7, 2021.

(51) Int. Cl.
*H04L 65/403* (2022.01)
*G06F 3/04842* (2022.01)
(Continued)

(52) U.S. Cl.
CPC ........ *H04L 65/403* (2013.01); *G06F 3/04842* (2013.01); *G16H 80/00* (2018.01); *H04L 65/1093* (2013.01)

(58) Field of Classification Search
CPC ... H04L 65/403; H04L 65/1093; G16H 80/00; G06F 3/04842
See application file for complete search history.

(56) References Cited

U.S. PATENT DOCUMENTS 9,160,967 B2 * 10/2015 Wang ............... H04M 3/56
9,569,431 B2 * 2/2017 Uszkoreit ............... H04M 3/56
(Continued)

FOREIGN PATENT DOCUMENTS

CN 111639503 A * 9/2020 ............ G06F 40/47
CN 112738446 A * 4/2021
(Continued)

OTHER PUBLICATIONS

"How Does Zoom Interpretation work", Oct. 27, 2020, TranslatorUSA, pp. 1-4 (Year: 2020).*
(Continued)

*Primary Examiner* — Justin R. Blaufeld
(74) *Attorney, Agent, or Firm* — Womble Bond Dickinson (US) LLP

(57) ABSTRACT

A method and system for adding a language interpreter to a video call between a healthcare provider and a patient is provided. The method includes initiating the video call between a healthcare provider device and a patient device. Communication information of a language interpreter device can be received and used to call the language interpreter device. The language interpreter device may be added to the video call to allow the language interpreter to facilitate communication between the healthcare provider and the patient. Other embodiments are described and claimed.

16 Claims, 5 Drawing Sheets

(51) Int. Cl.
  *G16H 80/00* (2018.01)
  *H04L 65/1093* (2022.01)

(56) References Cited

U.S. PATENT DOCUMENTS

| | | | | |
|---|---|---|---|---|
| 9,992,342 | B1* | 6/2018 | Yarnell | H04M 3/5183 |
| 10,616,278 | B1* | 4/2020 | Johansson | G06F 40/134 |
| 2003/0073430 | A1* | 4/2003 | Robertson | H04M 1/27475 |
| | | | | 455/566 |
| 2004/0235520 | A1* | 11/2004 | Cadiz | H04M 19/042 |
| | | | | 455/557 |
| 2005/0251421 | A1* | 11/2005 | Chang | G16H 40/20 |
| | | | | 705/2 |
| 2007/0167153 | A1* | 7/2007 | Cho | H04M 1/57 |
| | | | | 455/414.1 |
| 2014/0080465 | A1* | 3/2014 | Cho | H04M 1/724 |
| | | | | 455/566 |
| 2014/0108055 | A1 | 4/2014 | Phillips | |
| 2014/0132701 | A1* | 5/2014 | Wang | H04L 12/1827 |
| | | | | 348/14.08 |
| 2014/0273984 | A1* | 9/2014 | Aerrabotu | H04M 1/2746 |
| | | | | 455/414.1 |
| 2015/0347399 | A1* | 12/2015 | Aue | H04M 3/42 |
| | | | | 704/2 |
| 2016/0170970 | A1* | 6/2016 | Lindblom | G10L 21/003 |
| | | | | 704/3 |
| 2016/0203127 | A1* | 7/2016 | Uszkoreit | G10L 15/005 |
| | | | | 704/277 |
| 2016/0284202 | A1* | 9/2016 | Traughber | G16H 80/00 |
| 2018/0039623 | A1* | 2/2018 | Ahn | G10L 15/26 |
| 2018/0103073 | A1* | 4/2018 | Rosenberg | H04L 61/4555 |
| 2018/0262619 | A1* | 9/2018 | Yarnell | H04M 3/5125 |
| 2021/0335502 | A1* | 10/2021 | Cordell | G06F 40/58 |
| 2021/0351946 | A1* | 11/2021 | Chanda | H04L 12/1818 |
| 2022/0301727 | A1* | 9/2022 | Miranda | G16H 80/00 |

FOREIGN PATENT DOCUMENTS

KR    101877850 B1 *  7/2018
WO    WO-2022093345 A1 *  5/2022

OTHER PUBLICATIONS

"How to Enable Live Translation During Skype Calls", May 28, 2020, ARALINGUA, pp. 1-2 (Year: 2020).*

Greg Marshall, "For Calls to Family, Here'sHow Doctors Can Get anInterpreter on the Line", Apr. 21, 2020, pp. 1-9 (Year: 2020).*

"Accessing Interpreters for Telehealth is Easy with 3-Way Video Calls", Sep. 22, 2020, pp. 1-5 (Year: 2020).*

AMN Healthcare Language Services "Stratus Video & Zoom", Oct. 10, 2019, 2 pages, URL: https://player.vimeo.com/video/365626801.

The Languageline Solutions Team: "How to Add an Interpreter to a Telehealth Zoom call", Oct. 31, 2020, 5 pages, URL: https://blog.languageline.com/how-to-add-an-interpreter-to-a-telehealth-zoom-call.

"Zoom: How to Add an On-Demand Interpreter to a Virtual Meeting", Oct. 31, 2020, 7 pages, URL: https://www.languageline.com/download-zoom-how-to-add-an-on-call-interpreter-to-a-virtual-meeting.

Arizona Supreme Court, Administrative Office of the Courts "Using the Language Interpretation Feature in Zoom", Jun. 30, 2020, cover page and pp. 1-20, URL: https://www.courts.wa.gov/content/publicUpload/Interpreters/Arizona%20ZoomInterpretingFeatureGuide.pdf.

The International Search Report and Written Opinion of the International Searching Authority for PCT Application No. PCT/US2022/023530 mailed Jul. 13, 2022, 15 pages.

* cited by examiner

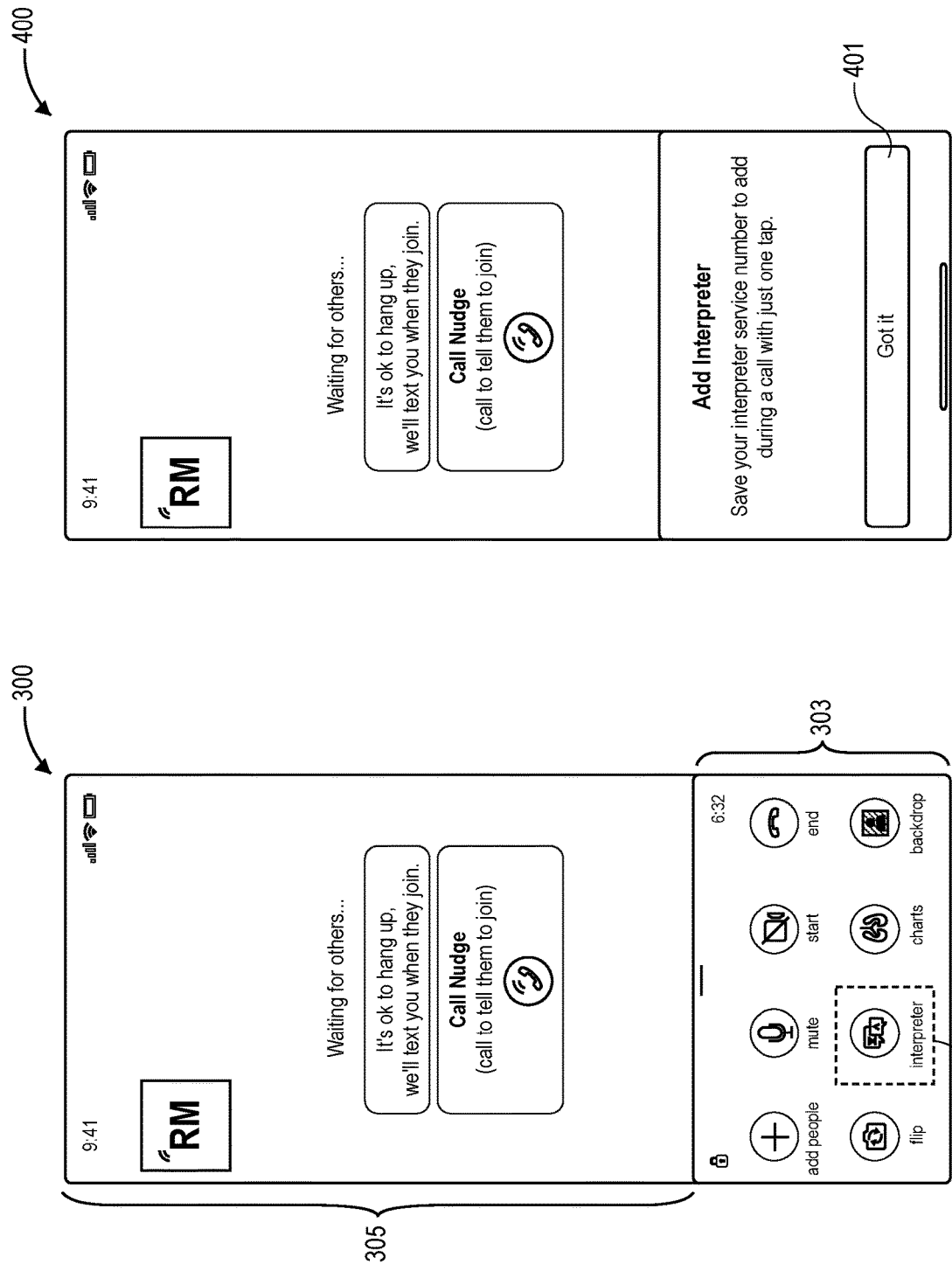

US 12,028,387 B2

METHOD OF ADDING LANGUAGE INTERPRETER DEVICE TO VIDEO CALL

RELATED APPLICATIONS

This application claims priority from and the benefit of U.S. Provisional Patent Application No. 63/171,851 filed on Apr. 7, 2021, the entire contents of which are incorporated herein by reference in their entirety.

TECHNICAL FIELD

This disclosure generally relates to video calls. In particular, this disclosure relates to adding language interpreters to video calls between healthcare providers and patients.

BACKGROUND

Healthcare providers (e.g., doctors, nurses, etc.) may provide various health related services and products to patients. Patients may often visit health care facilities (e.g., hospitals, clinics, etc.) to receive the health related services and products. For example, a patient may visit a clinic or a hospital for a checkup or to speak with a doctor about a particular medical/health issue.

BRIEF DESCRIPTION OF THE DRAWINGS

Embodiments and implementations of the present disclosure will be understood more fully from the detailed description given below and from the accompanying drawings of various aspects and implementations of the disclosure, which, however, should not be taken to limit the disclosure to the specific embodiments or implementations, but are for explanation and understanding only.

FIGS. 3-6 show examples of user interfaces in accordance with one or more embodiments of the disclosure.

DETAILED DESCRIPTION

As discussed above, patients often visit healthcare professionals at physical locations to receive health related services and/or products. As healthcare continues to evolve, more efficient and/or convenient methods of providing health related services and/or products may be used. For example, rather than visiting a healthcare professional in person, it may be more convenient to have a video call (e.g., a video conference) between a healthcare professional and a user. However, a user may not be proficient in the use of computing devices and/or applications for joining or setting up video calls. For example, some patients may have more difficulty typing in an identifier for a video call and a password for the video call. Thus, an easier and/or more efficient method of joining or setting up a video call between a patient and a healthcare professional may be useful.

In some instances, a user (e.g., a patient) and a healthcare provider (e.g., a physician) may speak different languages. Video calls could benefit from having a language interpreter present in the call, so that the user and healthcare provider may communicate with each other. As such, a method can include adding or introducing a language interpreter into the video call between the user and the healthcare provider. Adding or introducing the interpreter can include: providing a video call that includes a healthcare provider device and a user device; receiving communication information of a language interpreter device from the healthcare provider device; calling the language interpreter device using the communication information; and joining the language interpreter device to the video call.

Figure 1:
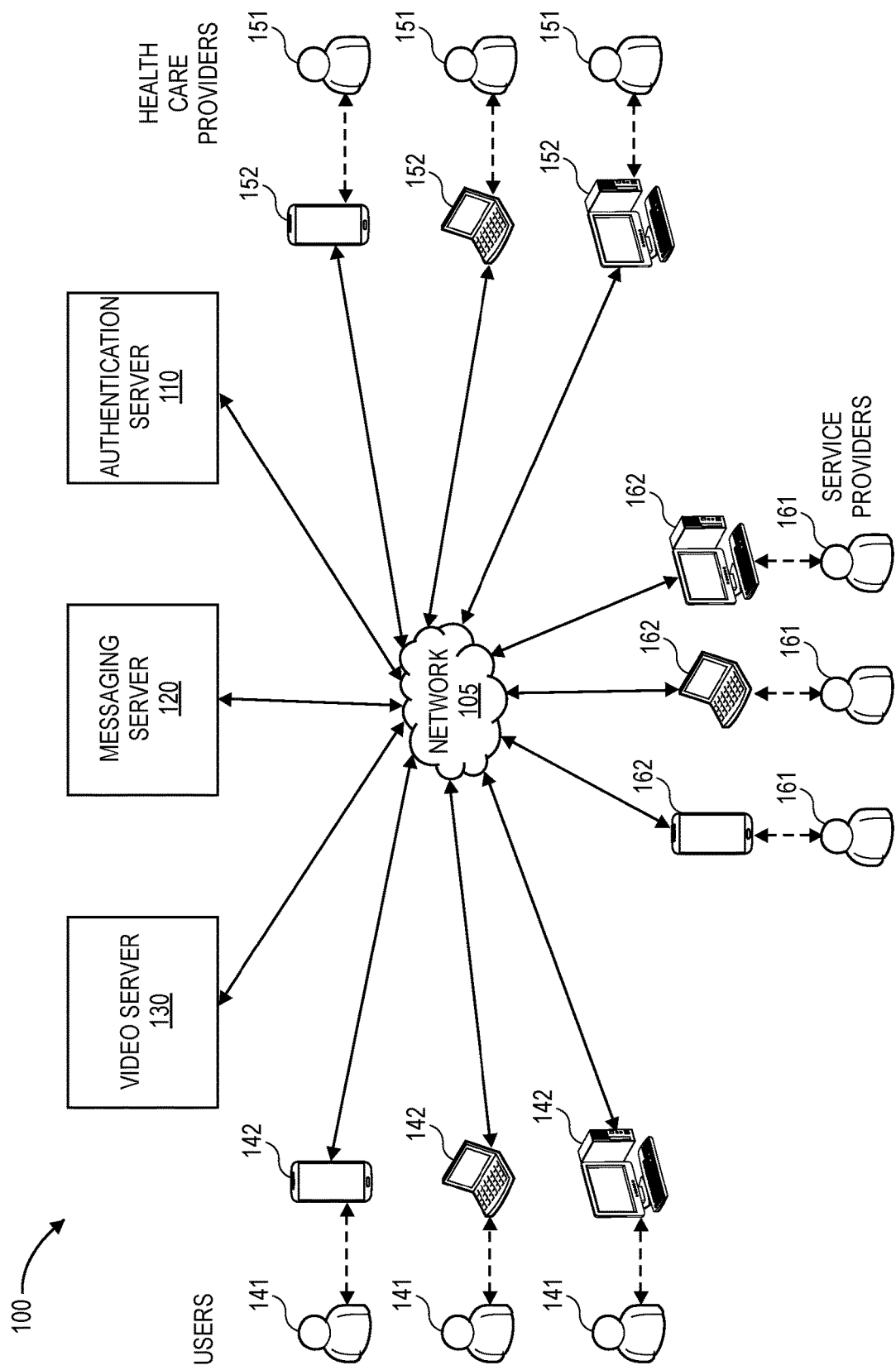
FIG. 1 is a diagram illustrating an example network architecture in accordance with one or more embodiments of the disclosure.

FIG. 1 is a diagram illustrating an example network architecture, in accordance with one or more embodiments of the disclosure. A network architecture 100 includes a network 105, an authentication server 110, a messaging server 120, a video server 130, users 141, computing devices 142, healthcare providers 151, computing devices 152, service providers 161, and computing devices 162.

In one embodiment, the users 141 may be patients who use services and/or products provided by one or more of the healthcare providers 151 or service providers 161. Each user 141 may use a computing device 142 to communicate with one or more of a healthcare provider 151 and a service provider 161. Examples of computing devices 142 may include, but are not limited to, a smartphone, a tablet computer, a laptop computer, a desktop computer, etc.

In one embodiment, the healthcare providers 151 may be people who provide health related services and/or products to the user. Examples of healthcare providers 151 may include, but are not limited to, doctors, pharmacists, dentists, nurses, therapists, psychologists, technicians, surgeons, etc. Each healthcare provider 151 may use a computing device 152 (e.g., smartphone, tablet computer, etc.) to communicate with one or more of the users 141 or the service providers 161.

In one embodiment, a service provider 161 may provide additional or ancillary services to one or more of the users 141 or the healthcare providers 151. Examples of service providers 151 may include, but are not limited to, interpreters (e.g., a language interpreter), insurance providers, billing specialists, etc. Each service provider 161 may use a computing device 162 (e.g., smartphone, tablet computer, etc.) to communicate with one or more of the users 141 or the healthcare providers 151.

As discussed above, a healthcare provider 151 (e.g., a doctor) may communicate with a user (e.g., a patient) via a video call (e.g., a video conference, a video meeting, etc.). The system architecture 100 may allow a healthcare provider 151 to provide a user 141 with a link that allows the user 141 to join or setup the video call with the healthcare provider 151. In one embodiment, the user 141 may be able to join or setup the video call without using video call details. For example, the link can allow the user 141 to join the video call without providing or using security credentials, such as a password, and/or without providing a meeting identifier.

In one embodiment, the authentication server 110 may authenticate one or more of the healthcare provider 151, a service provider 161, or a user 141. For example, a computing device 152 (used by the healthcare provider 151) may include a software application (e.g., an application, a program, etc.) that allows the healthcare provider 151 to join or setup the video call with the user 141. The app may prompt the healthcare provider 151 for a user name, password, or other security credentials before allowing the user to join or setup the video call. The software application may provide the security credentials to the authentication server 110 which may authenticate or verify the security credentials. After the security credentials of the healthcare provider 151 have been verified, the healthcare provider 151 may be allowed to setup or join the video call.

In one embodiment, the messaging server 120 may send or transmit the link to a computing device 142 of the user 141. For example, the healthcare provider 141 may setup the video call with the user via the software application on the computing device 152. The software application may communicate with the video server 130 and the video server 130 may communicate with the messaging server 120 to indicate that the healthcare provider 141 wants to setup the video call with the user 141. The messaging server 120 may transmit or send the link to the computing device 142 of the user 141. For example, the messaging server 120 may send a short message service (SMS) message containing the link to the computing device 142 of the user 141.

The messaging server 120 can be maintained by a same or different entity than that which maintains the video server 130. For example, the messaging server 120 may be maintained by an entity that provides communication tools for making and receiving phone calls, sending and receiving text messages, and performing other communication functions. The communication functions can be performed through web service application programming interfaces, for example.

In one embodiment, the video server 130 may host the video call between the healthcare provider 151 and the user 141. For example, after the user selects, clicks, activates, etc., the link, the computing device 142 may communicate with the video server 130 to setup or join the video call. The video call may forward data (e.g., video data, video frames, audio data, audio frames, etc.) between the computing device 142 (of the user 141) and the computing device 152 (of the user 151). The video server 130 may also allow different people to join or leave a video call. For example, the healthcare provider 151 may initiate the video call with the user 141. At a later point in time, the healthcare provider 151 may add a service provider 161, such as a language interpreter, to the video call. The video server 130 may forward data between the computing devices of the people who are added or removed from the video call.

In one embodiment, the link may allow the user 141 to join or setup the video call without providing or using security credentials, such as a password. For example, by selecting, clicking, activating, etc., the link, the computing device 142 of the user 141 may automatically setup or join a video call with the healthcare provider 151. The user 141 may not be prompted for security credentials to join or setup the video call.

In one embodiment, the link may include various portions or pieces of data. For example, the link may include one or more of a location of a server (e.g., the video server 130), one or more identifiers, a time period, and a signature. The link may allow the user 141 to join the video call without providing security credentials (e.g., without entering a password) and/or without providing an identifier for the meeting (e.g., a meeting ID, a meeting name, etc.). This may allow the user 141 to join the video call more quickly and/or easily.

Figure 2:
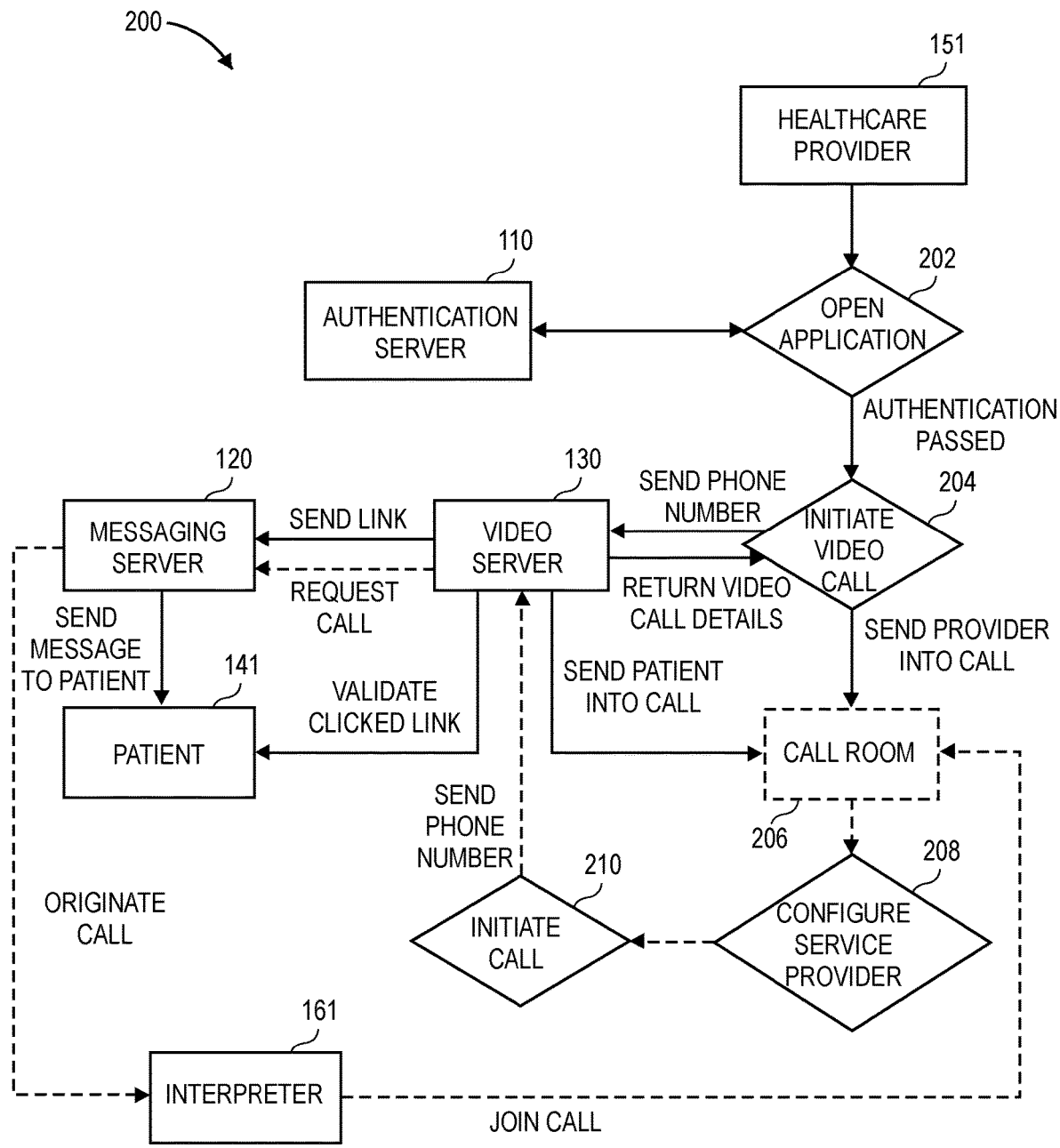
FIG. 2 is a flowchart of an example method of setting up a video call in accordance with one or more embodiments of the disclosure.

FIG. 2 is a flow diagram of a method of setting up a video call in accordance with one or more embodiments of the present disclosure. Process 200 may be performed by processing logic that may comprise hardware (e.g., circuitry, dedicated logic, programmable logic, a processor, a processing device, a central processing unit (CPU), a system-on-chip (SoC), etc.), software (e.g., instructions running/executing on a processor), firmware (e.g., microcode), or a combination thereof. In some embodiments, the process 200 may be performed by various computing devices, such as the authentication server 110, the messaging server 120, the video server 130, etc. The actions of the user 141 may be performed by a computing device of the user 141 (e.g., computing device 142 illustrated in FIG. 1), the actions of the healthcare provider 151 may be performed by a computing device of the healthcare provider 151 (e.g., computing device 152 illustrated in FIG. 1), and the actions of the service provider 161, e.g., the language interpreter, may be performed by a computing device of the service provider 161 (e.g., computing device 162 illustrated in FIG. 1).

The process 200 begins at block 202. The healthcare provider 151 (e.g., a doctor) may use, open, etc., a software application (e.g., an application, software, etc.) to setup or initiate a video call with the user 141 (e.g., a patient). The user 141 may be prompted for security credentials which may be provided to the authentication server 110 for verification or authentication. If the security credentials are verified, the application may, at block 204, initiate a video call. The application may communicate with the video server 130 to setup the video call, which the user may join at a later time. The healthcare provider 151 may also provide a phone number, email address, name, etc., of the user 141 so that the messaging server 120 is able to determine which user to send the message and/or link to.

The video server 130 may also communicate with the messaging server 120 to indicate that the healthcare professional 151 wants to setup a video call with the user 141. The messaging server 120 may transmit a message (e.g., an SMS message, a MMS message, a chat message, a text message, etc.) to the user 141 to indicate that the healthcare professional 151 wants to setup a video call with the user 141. The message may include a link that allows the user 141 to join the video call. The link may allow the user 141 to join the video call without providing security credentials (e.g., without entering a password). This may allow the user 141 to join the video call more quickly and/or easily.

In one embodiment, the link may include various portions or pieces of data. For example, the link may include one or more of a location of a server (e.g., the video server 130), one or more identifiers, a time period, and a signature. The link may allow the user 141 to join the video call without providing an identifier for the meeting (e.g., a meeting ID, a meeting name, etc.).

When the user 141 activates, clicks, selects, etc., the link, the user may automatically join the video call initiated by the healthcare professional 151. The user 141 may be connected to the video server 130 so that the video server 130 can allow the user 141 to join the video call with the healthcare provider 151. For example, at block 206, the video server 130 may place the healthcare provider 151 and the user 141 in a room (e.g., a call room, a video meeting room, a virtual room, etc.) to have the video call.

Through the network architecture described, a provider (e.g., a registered and verified healthcare professional) can initiate a call to a patient. The network architecture 100 includes network 105, an authentication server 110, a messaging server 120, a video server 130, users 141, computing devices 142, healthcare providers 151, computing devices 152, service providers 161, and computing devices 162.

In some embodiments, the network architecture allows the healthcare provider 151 to add a service provider 161, e.g., a language interpreter, to the video call. For example, the healthcare provider 151 may have difficulty understanding a native language of the user 141, and may desire the assistance of the language interpreter to facilitate communications with the user 141. The process of adding the language interpreter is illustrated in FIG. 2 using dotted lines indicating the flow of operations after the video call is initiated. Furthermore, the operations illustrated in FIG. 2 may be carried out through the examples of user interfaces shown in FIGS. 3-6, and thus, FIGS. 2-6 are referred to in combination below.

Still referring to FIG. 2, at block 208, one or more interpreter services are configured. The configuration of interpreter services can be at an individual or at an enterprise level. More particularly, an individual healthcare provider 151, e.g., a physician, can configure the interpreter service by storing communication information for the interpreter service in a memory of the video server 130. Alternatively, an enterprise healthcare provider 151, e.g., a medical group, hospital, etc., which the physician is a member of, can configure the interpreter service. The enterprise can store the communication information for the interpreter service in the memory of the video server 130. Accordingly, the communication information can be pre-stored and accessed by any member of the enterprise through a device 152 communicating with the video server 130.

The healthcare provider 151 can configure the interpreter service 161 before or during the video call. To configure the service provider, the healthcare provider 151 can specify communication information of the interpreter service 161. The communication information may include, for example, a name and/or a telephone number of the interpreter service (or of an individual language interpreter). Communication information may alternatively or additionally include a URL, IP address, etc., which can be used to contact the interpreter service through the messaging server 120. The communication information can be stored in computer readable memory, for example, as a setting. This setting can be accessible to nodes on the network (e.g., the authentication server 110, messaging server 120, video server 130, computing devices 142, computing devices 152, and/or computing devices 162. Accordingly, during the video call, the healthcare provider device 152 can use the communication information to contact and add the language interpreter device 162 to the video call, so the language interpreter 151 can be present on the call with the healthcare provider 151 and a user 141.

Referring to FIG. 3, an example user interface is shown in accordance with one or more embodiments of the disclosure. A user interface 300 can be used by the healthcare provider 151 to configure and/or add a language interpreter to the video call. The healthcare provider 151 can interact with the user interface 300 through a touchscreen display, a peripheral device (e.g., mouse, keyboard), or other equivalent input technology. The user interface 300 can be integral to or supported by a computing device (e.g., 152) operated by the healthcare provider 151.

The healthcare provider 151 who initiated the video call can set up the interpreter service prior to, or during an active call. For example, the user interface 300 can include an interpreter user interface element 301 that is accessible through the user interface 300. More particularly, the user interface 300 can include a menu 303 in a drawer region of the user interface 300. The menu 303 contains one or more user interface elements to allow the healthcare provider to take certain actions during the video call. The drawer region can be a region separate and set apart from, e.g., below, a video display region 305. The video display region 305 can be a portion of the user interface 300 that displays participants during the video call. User interface elements within the menu 303 may include, e.g., an "add people" button to add additional users 141 to the video call. Other participants (additional users 141) who may be added include family members or colleagues. The menu 303 may also include a "mute" button to mute audio on the call, a "start" button to allow video to be started or stopped, an "end" button to terminate the call, etc.

In an embodiment, the interpreter user interface element 301 includes a button or text field labeled "interpreter." The button 301 allows the healthcare provider 151 to add an interpreter 161 to the video call. The interpreter user interface element 301, as well as the other user interface elements shown in the figures, can be selectable text, a graphical button, or another area of the user interface that allows a user to provide an input.

FIG. 4 shows an example user interface in accordance with one or more embodiments of the disclosure. In response to a user selection of the interpreter user interface element 301 in the drawer area region of the user interface 300, a user interface 400 may be displayed. The user interface 400 can include a confirmation user interface element 401. The confirmation user interface element 401 can be a selectable button or text field. When selected by the healthcare provider 151, the user interface element 401 can confirm that the healthcare provider 151 intends to add the language interpreter to the video call. More particularly, selection of the user interface element 401 confirms that the healthcare provider 151 wishes to save an interpreter service 161 for use in adding the language interpreter during the video call. The language interpreter may, for example, be added by a single tap of a user interface element designating or indicating the language interpreter, as described below.

Figure 5:
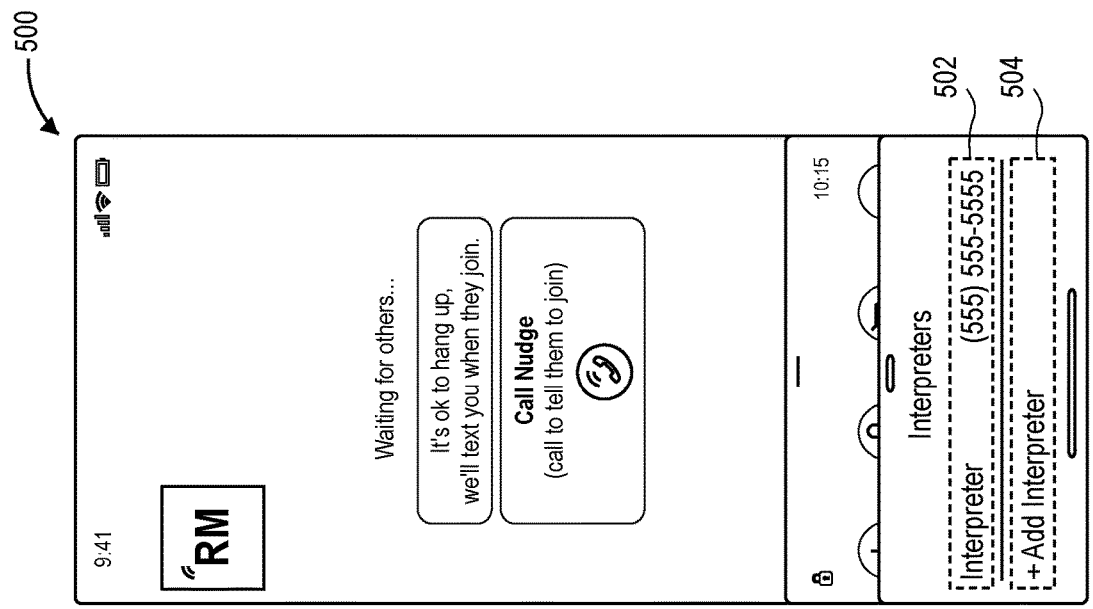

Referring to FIG. 5, an example user interface is shown in accordance with one or more embodiments of the disclosure. In response to selection of the confirmation user interface element 401, the user interface 400 can transition to a user interface 500. The user interface 500 can include an interpreter selection user interface element 502. The user interface element 502 is associated with a configured interpreter service 161. More particularly, the interpreter user interface element 502 can indicate the communication information that was previously stored for the interpreter service. The communication information may have been stored in a backend server that is referenced by the video server 130 to add the interpreter to the video call. More particularly, the communication information may have been previously entered by the physician individually, or by the enterprise of the physician, and saved in the backend server for use during future sessions. Accordingly, the language interpreter communication information can be accessed by the physician through any session that the physician is logged into, whether the session is carried out through a device 142 that was used to enter the information, e.g., a tablet, or another device that is used to initiate the video call, e.g., a desktop computer.

The user interface 500 can also include an interpreter addition user interface element 504. The user interface element 504 can be a selectable button or text field indicating to the physician 151 the option to configure and add a new (not a pre-stored) interpreter service device to the video call. The user interface element 504 may be labeled, for example, "add interpreter."

Figure 6:
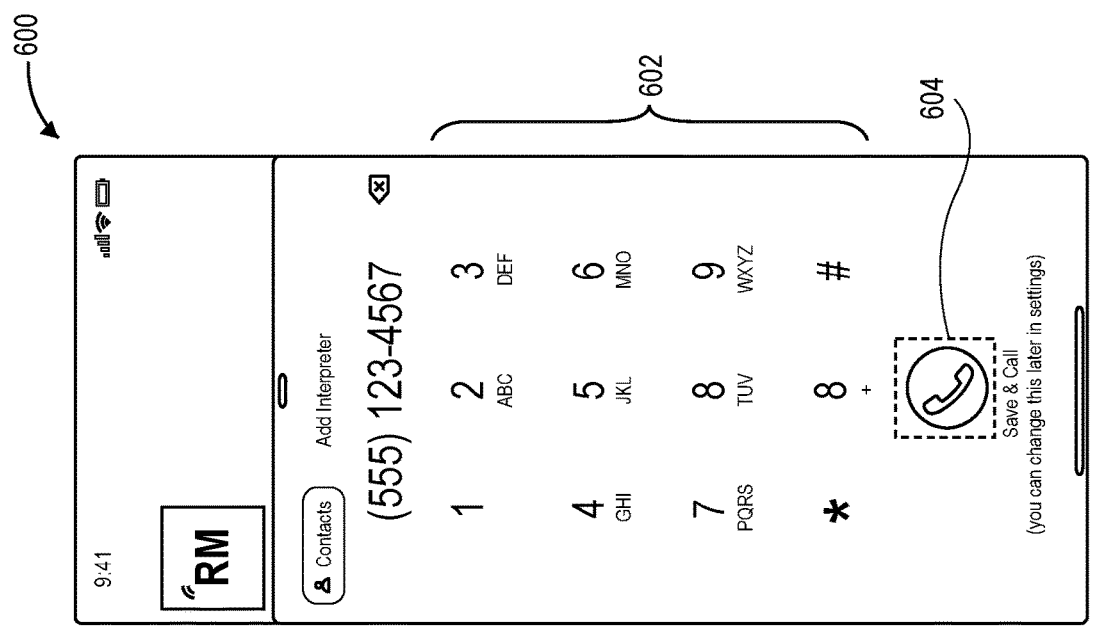

Referring to FIG. 6, an example user interface is shown in accordance with one or more embodiments of the disclosure. In response to selection of the interpreter addition user interface element 504, the user interface 600 may be displayed on the healthcare provider device 152. The user interface 600 allows the healthcare provider 151 to configure and/or edit the communication information of an interpreter service. For example, the healthcare provider 151 can input a telephone number through an input dial pad 602. The dial pad can include buttons representing digits to allow for entry of the phone number. In other embodiments, the user interface 600 can include an alphanumeric keyboard that allows a user to specify the communication information that is stored in association with an interpreter service. The user can therefore input alphanumeric communication information such as a phone number, URL, IP address, or other addressing information that can be used to reach the interpreter service provider. Input can be received through graphical user interface (GUI) keypads, GUI forms, keyboards, a mouse, or other digital input devices. The communication information can be stored electronically and accessed for use during a call with the user, thus configuring the interpreter service.

Configuration of the new interpreter can be performed prior to, during, or after a call. More particularly, the healthcare provider (the physician or an enterprise representative) can access the user interface 600 through the application to configure the interpreter service 161. The configuration information for the service can be entered and stored in settings that are associated with the application (e.g., as application preferences) and can be local to a computing device (e.g., computing device 152) and/or stored on a network connected server (e.g., servers 130, 120, 110).

In an embodiment, a save user interface element 604, e.g., a button and/or text field, can be used to save the communication information of the interpreter and/or call the interpreter service device 162. More particularly, a user selection of the save user interface element 604 after entering the communication information can cause the communication information of the new interpreter service to be stored in the backend server for access by a system server, e.g., the video server 130.

Referring again to FIG. 2, at block 210, the healthcare provider device 152 can initiate a call to the interpreter service device 162. Once an interpreter service has been configured, the interpreter service becomes available during the active call and/or subsequent calls. Initiation of the call to the pre-configured or currently configured interpreter service can be performed through user interface 500 and/or user interface 600.

Referring again to FIG. 5, one of the interpreter selection user interface elements 502 can be selected through a user selection to initiate the call to the indicated interpreter. For example, selection of the illustrated user interface element 502 can initiate the call to the interpreter at the telephone number ending in "5555." Selection of the user interface element 502 can be through a single tap on the user interface 500. Accordingly, the selection and initiation of a call to a pre-configured interpreter service 161 can be performed quickly, in real-time while the physician 151 is on the video call with the patient 141.

Referring again to FIG. 6, the saved user interface element 604 can be selected to initiate the call to the new interpreter service. For example, selection of the illustrated user interface element 604 can both save the settings for the configured interpreter, and can initiate the call to the interpreter at the telephone number ending in "4567."

In response to selection of the user interface element 502 or 604, the stored communication information of the configured interpreter service is called upon to add the interpreter service to the call. When the call to the interpreter is initiated, the phone number of the selected interpreter can be sent to the video server 130. The video server 130 can then request that a call be originated by the messaging server 120. In response to receiving the request from the video server 130, the messaging server 120 can originate a call to the interpreter 161 using the telephone number.

When the call is originated to the interpreter service device 162, and the interpreter 161 answers the call, the interpreter service can join or be added to the active telehealth call in the call room as an additional participant. For example, the interpreter 161 may be added as an audio only participant to the call, and may be able to communicate with the healthcare provider 151 and patient 141 who are both in the call room. Alternatively, the interpreter may be added as an audio and video participant. For example, the interpreter 161 may be sent into the call room by the video server 130. In some embodiments, the interpreter 161 can be sent a link, e.g., through the messaging server 120 in a manner similar to that used to set up the call room with the patient 141. The interpreter 161 can select, or click on, the link to validate with the video server 130 and be sent into the call room. In either case, the interpreter can help facilitate discussion between the user 141 and the healthcare provider 151, for example, translating languages back and forth.

Figure 7:
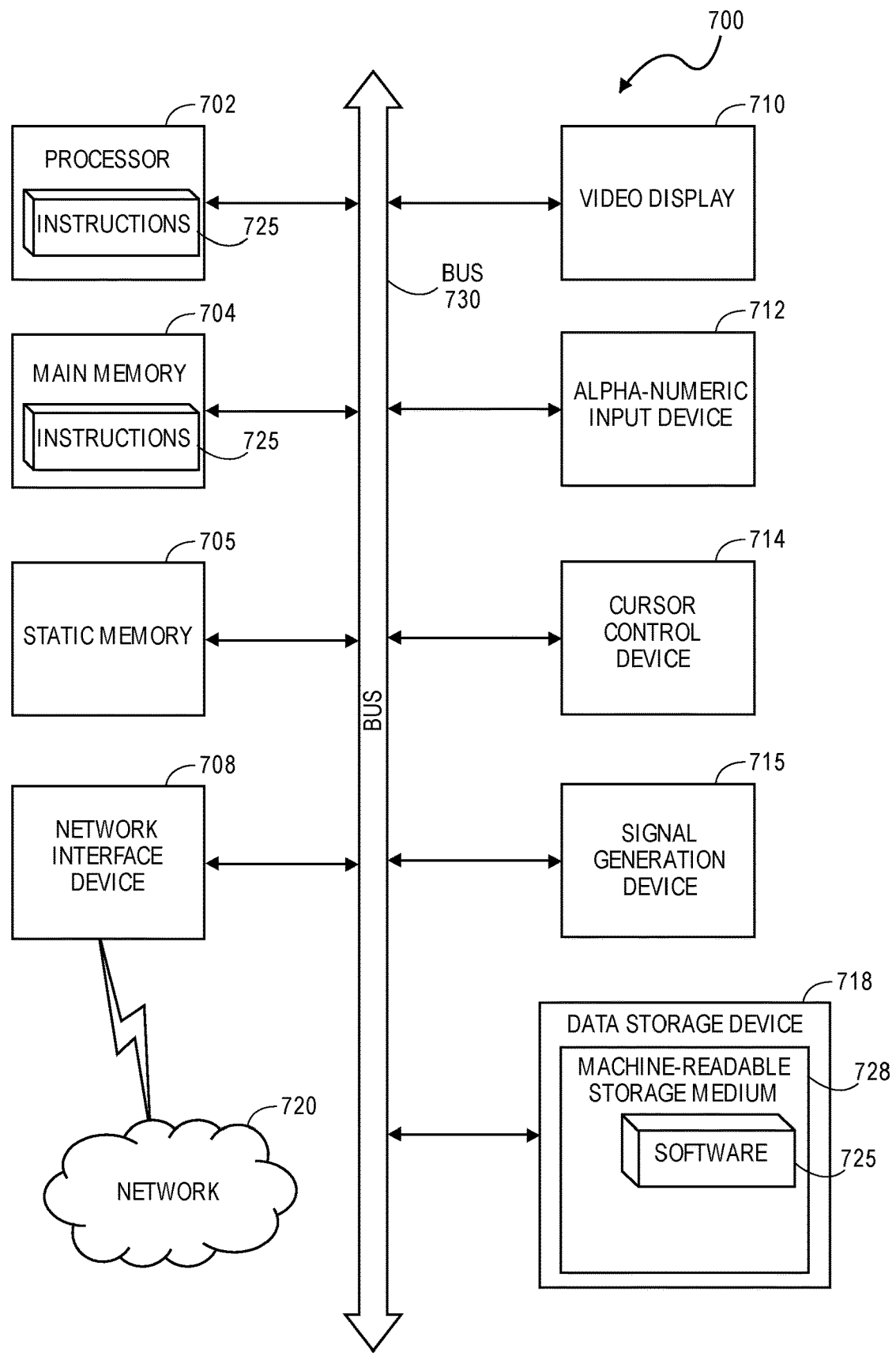
FIG. 7 is a block diagram of an example computing device that may perform one or more of the operations described herein, in accordance with some embodiments

Referring to FIG. 7, a block diagram of an example computing device that may perform one or more of the operations described herein is shown in accordance with some embodiments. More particularly, computing device 700 may be integrated in any of the servers and/or devices described above to perform any of the described operations. Computing device 700 may be connected to other computing devices in a LAN, an intranet, an extranet, and/or the Internet. The computing device may operate in the capacity of a server machine in the client-server network environment or in the capacity of a client in a peer-to-peer network environment. The computing device may be provided by a personal computer (PC), a set-top box (STB), a server, a network router, switch or bridge, or any machine capable of executing a set of instructions (sequential or otherwise) that specify actions to be taken by that machine. Further, while only a single computing device is illustrated, the term "computing device" shall also be taken to include any collection of computing devices that individually or jointly execute a set (or multiple sets) of instructions to perform the methods discussed herein.

The example computing device 700 may include one or more processors (e.g., a processing device, a general purpose processor, a PLD, etc.) 702, a main memory 704 (e.g., synchronous dynamic random access memory (DRAM), read-only memory (ROM)), a static memory 705 (e.g., flash memory and a data storage device 718), which may communicate with each other via a bus 730.

The one or more processors 702 may be provided by one or more general-purpose processing devices such as a microprocessor, central processing unit, or the like. In an illustrative example, processor(s) 702 may comprise a complex instruction set computing (CISC) microprocessor, reduced instruction set computing (RISC) microprocessor, very long instruction word (VLIW) microprocessor, or a processor implementing other instruction sets or processors implementing a combination of instruction sets. Processor(s) 702 may also comprise one or more special-purpose processing devices such as an application specific integrated circuit (ASIC), a field programmable gate array (FPGA), a digital signal processor (DSP), network processor, or the like. The processor(s) 702 may be configured to execute the operations described herein, in accordance with one or more aspects of the present disclosure, for performing the operations and steps discussed herein.

Computing device 700 may further include a network interface device 708 which may communicate with a network 720. The computing device 700 also may include a video display unit 710 (e.g., a liquid crystal display (LCD) or a cathode ray tube (CRT)), an alphanumeric input device 712 (e.g., a keyboard), a cursor control device 714 (e.g., a mouse) and an acoustic signal generation device 715 (e.g., a speaker). In one embodiment, video display unit 710, alphanumeric input device 712, and cursor control device 714 may be combined into a single component or device (e.g., an LCD touch screen).

Data storage device 718 may include a computer-readable storage medium 728 on which may be stored one or more sets of instructions 725 that may include instructions for carrying out the operations described herein, in accordance with one or more aspects of the present disclosure. Instructions 725 may also reside, completely or at least partially, within main memory 704 and/or within processor(s) 702 during execution thereof by computing device 700, main memory 704 and processor(s) 702 also constituting computer-readable media. The instructions 725 may further be transmitted or received over a network 720 via network interface device 708.

While computer-readable storage medium 728 is shown in an illustrative example to be a single medium, the term "computer-readable storage medium" should be taken to include a single medium or multiple media (e.g., a centralized or distributed database and/or associated caches and servers) that store the one or more sets of instructions. The term "computer-readable storage medium" shall also be taken to include any medium that is capable of storing, encoding or carrying a set of instructions for execution by the machine and that cause the machine to perform the methods described herein. The term "computer-readable storage medium" shall accordingly be taken to include, but not be limited to, solid-state memories, optical media and magnetic media.

The foregoing description, for the purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the embodiments and its practical applications, to thereby enable others skilled in the art to best utilize the embodiments and various modifications as may be suited to the particular use contemplated. Accordingly, the present embodiments are to be considered as illustrative and not restrictive, and the invention is not to be limited to the details given herein, but may be modified within the scope and equivalents of the appended claims.

What is claimed is:

1. A method, comprising:
   initiating a video call between a healthcare provider device and a patient device;
   receiving a user selection of a save user interface element requesting to both add a language interpreter device to the video call and store communication information of the language interpreter device;
   initiating, in response to the user selection, a call to the language interpreter device using the communication information, wherein initiating the call causes a message to be sent to the language interpreter device, and wherein the message comprises a link to allow the language interpreter device to join the video call without a user of the language interpreter device inputting video call details;
   storing, in response to the user selection, the communication information in a set of communication information containing exclusively communication information associated with one or more interpreter service devices, wherein the communication information is stored for future access through an interpreter user interface element during a telehealth call;
   receiving, at the language interpreter device, a selection of the link;
   joining the language interpreter device to the video call in response to the language interpreter device receiving the selection of the link;
   receiving a second user selection of the interpreter user interface element during the telehealth call; and
   displaying, in response to the second user selection of the interpreter user interface element during the telehealth call, a listing of one or more interpreter selection user interface elements associated with the one or more interpreter service devices including the language interpreter device, wherein the listing does not include communication information associated with the patient device.

2. The method of claim 1, wherein the user selection is received from the healthcare provider device.

3. The method of claim 1 further comprising receiving a third user selection of the interpreter selection user interface element associated with the language interpreter device on the healthcare provider device, wherein the interpreter selection user interface element indicates one or more of a name or a telephone number associated with the language interpreter device.

4. The method of claim 3, wherein the third user selection of the interpreter selection user interface element is a single tap on the interpreter selection user interface element associated with the language interpreter device.

5. The method of claim 1 further comprising displaying the save user interface element in response to a fourth user selection of an interpreter addition user interface element on the healthcare provider device.

6. The method of claim 1, wherein initiating the video call comprises:
   receiving a request to initiate the video call,
   generating the video call based on the request,
   generating a second message comprising a second link to the video call, wherein the second link allows the patient device to join the video call without using the video call details, and
   sending the message comprising the second link to the patient device.

7. A system comprising:
   a memory to store instructions; and
   one or more processing devices configured to execute the instructions to cause the system to:
      initiate a video call between a healthcare provider device and a patient device,
      receive a user selection of a save user interface element requesting to both add a language interpreter device to the video call and store communication information of the language interpreter device,
      initiate, in response to the user selection, a call to the language interpreter device using the communication information, wherein initiating the call causes a message to be sent to the language interpreter device, and wherein the message comprises a link to allow the language interpreter device to join the video call without a user of the language interpreter device inputting video call details;

store, in response to the user selection, the communication information in a set of communication information containing exclusively communication information associated with one or more interpreter service devices, wherein the communication information is stored for future access through an interpreter user interface element during a telehealth call, join the language interpreter device to the video call in response to the language interpreter device receiving a selection of the link, and display, in response to a second user selection of the interpreter user interface element during the telehealth call, a listing of one or more interpreter selection user interface elements associated with the one or more interpreter service devices including the language interpreter device, wherein the listing does not include communication information associated with the patient device.

8. The system of claim 7, wherein the user selection is received from the healthcare provider device.

9. The system of claim 7, wherein the instructions further cause the system to receive a third user selection of the interpreter selection user interface element associated with the language interpreter device on the healthcare provider device, wherein the interpreter selection user interface element indicates one or more of a name or a telephone number associated with the language interpreter device.

10. The system of claim 7, wherein the instructions further cause the system to display the save user interface element in response to a fourth user selection of an interpreter addition user interface element on the healthcare provider device.

11. The system of claim 7, wherein to initiate the video call, the instructions cause the system to:
receive a request to initiate the video call,
generate the video call based on the request,
generate a second message comprising a second link to the video call, wherein the second link allows the patient device to join the video call without using the video call details, and
send the message comprising the second link to the patient device.

12. A non-transitory computer readable storage medium storing instructions executable by one or more processing devices of a system to cause the system to:
initiate a video call between a healthcare provider device and a patient device;
receive a user selection of a save user interface element requesting to both add a language interpreter device to the video call and store communication information of the language interpreter device;
initiate, in response to the user selection, a call to the language interpreter device using the communication information, wherein initiating the call causes a message to be sent to the language interpreter device, and wherein the message comprises a link to allow the language interpreter device to join the video call without a user of the language interpreter device inputting video call details;
store, in response to the user selection, the communication information in a set of communication information containing exclusively communication information associated with one or more interpreter service devices, wherein the communication information is stored for future access through an interpreter user interface element during a telehealth call;
join the language interpreter device to the video call in response to the language interpreter device receiving a selection of the link; and
display, in response to a second user selection of the interpreter user interface element during the telehealth call, a listing of one or more interpreter selection user interface elements associated with the one or more interpreter service devices including the language interpreter device, wherein the listing does not include communication information associated with the patient device.

13. The non-transitory computer readable storage medium of claim 12, wherein the user selection is received from the healthcare provider device.

14. The non-transitory computer readable storage medium of claim 12, wherein the instructions further cause the system to receive a third user selection of the interpreter selection user interface element associated with the language interpreter device on the healthcare provider device, wherein the interpreter selection user interface element indicates one or more of a name or a telephone number associated with the language interpreter device.

15. The non-transitory computer readable storage medium of claim 12, wherein the instructions further cause the system to display the save user interface element in response to a fourth user selection of an interpreter addition user interface element on the healthcare provider device.

16. The non-transitory computer readable storage medium of claim 12, wherein to initiate the video call the instructions cause the system to:
receive a request to initiate the video call,
generate the video call based on the request,
generate a second message comprising a second link to the video call, wherein the second link allows the patient device to join the video call without using the video call details, and
send the second message comprising the second link to the patient device.

* * * * *